United States Patent [19]

Gordon

[11] Patent Number: 5,166,132
[45] Date of Patent: Nov. 24, 1992

[54] HEALING COMPOSITION EMPLOYING AN ENZYME-MODIFIED CASEIN

[76] Inventor: Arthur L. Gordon, 109 Phaeton Dr., Wheeling, Ill. 60090

[21] Appl. No.: 327,743

[22] Filed: Mar. 23, 1989

[51] Int. Cl.⁵ .............................................. A61K 37/16
[52] U.S. Cl. .......................................... 514/2; 514/21; 424/DIG. 13; 530/360; 530/361; 530/832; 530/833
[58] Field of Search ....... 514/2, 21; 424/80, DIG. 13; 530/360, 361, 832, 833

[56] References Cited

U.S. PATENT DOCUMENTS 3,558,770  1/1971  Gordon et al. ................... 424/80

OTHER PUBLICATIONS

Scopes, Protein Purification, 1982, Springer–Verlag, New York, pp. 40–42.
Forbes, Beyond the Band–Aid, Jun. 1, 1987, Science & Technology.

*Primary Examiner*—Douglas W. Robinson
*Assistant Examiner*—Jean C. Witz
*Attorney, Agent, or Firm*—James R. Young

[57] ABSTRACT

A topical use pharmaceutical composition and a process for its preparation, comprising an improved enzyme-modified casein sol. Prior to being enzyme-modified, the casein is solubilized and neutralized by an alkali solution containing a molar weight percent ratio in the range of from 90:10 to 100:0, potassium hydroxide to sodium hydroxide. Said neutralization occurring for a time in the range of 5 to 35 minutes to allow for complete neutralization of the casein. The neutralized casein is then hydrolyzed or modified by enzymatic digestion by a proteolytic enzyme for a time sufficient to achieve a weight ratio of protein nitrogen to amino nitrogen in the range from 7:1 to 9:1. The improved enzyme-modified casein sol may then be mixed with stabilizing and pressuring agents, such as carrageenan, polyvinyl pyrrolidone, methyl paraben or propyl paraben. Topical uses for the improved enzyme-modified casein composition include healing and relieving infections, wounds, burns, dermatitis, skin eruptions, dandruff, hemorrhoids and bruises.

10 Claims, No Drawings

HEALING COMPOSITION EMPLOYING AN ENZYME-MODIFIED CASEIN

BACKGROUND OF THE INVENTION

1. Field of the Invention

This present invention relates generally to compositions for pharmaceutical uses and more specifically to pharmaceutical compositions of proteins and related polypeptides used to heal maladies occurring at or near the skin surface.

2. Description of the Prior Art

Some of the healing properties of colloidal compositions containing casein, carrageenan or polyvinyl pyrrolidone (PVP) have been long known. Casein, which is a series of related phosphoproteins, occurs naturally in bovine milk to the extent of about 3%. Casein is commonly produced through various means of precipitating the casein curd from the milk. One of the unique features of casein is that it contains all of the amino acids found in living tissue. When degraded with zinc acetate, casein has been used as a burn ointment.

Carrageenan is a naturally occurring structural polysaccharide found in red seaweed. Although one of its chief uses is as a gelling agent, it has been reported to stimulate connective tissue growth, which is essential in scar tissue formation.

PVP was originally developed in Germany during World War II as a blood plasma extender, but it currently has numerous applications in the pharmaceutical, cosmetic and food industries. PVP has been found to render various toxic materials less active due to its ability to form larger complexes with these toxic materials.

Some of these healing and related properties of casein, carrageenan, and PVP were brought together in research conducted by this inventor and Sam Weisberg, which culminated in U.S. Pat. No. 3,558,770. In this U.S. Pat. No. 3,558,770, we disclosed casein neutralized with potassium hydroxide (KOH) for 10 to 15 minutes and then hydrolyzed with a proteolytic enzyme. This enzyme-modified casein was then freeze dried, pulverized, reconstituted, and mixed with suspending, stabilizing, and perservative agents, such as carrageenan, PVP, and methyl pavasept. This enzyme-modified casein sol was found to be very effective as a wrinkle remover and a healing agent in the treatment of wounds resulting from traumatic injuries; healing such wounds, for example, in 4-5 days.

Since the time of U.S. Pat. No. 3,558,770, which issued in 1971, much of the focus in wound healing, beyond antiseptics, bandages or skin grafts, has been in synthesizing proteins known as growth factors. With genetic engineering techniques, scientists have been able to produce some of these naturally occurring growth factor proteins, which have potential in the treatment of wounds resulting from traumatic injuries or burns.

As effective as the pharmaceutical compositions of U.S. Pat. No. 3,558,770 and those cloned through genetic engineering are, i.e., healing in 4 to 6 days as opposed to the normal 7 to 10 days, they do have certain disadvantages. For example, they require a great deal of time and/or money to produce and they tend to be somewhat limited and specific in their applications.

SUMMARY OF THE INVENTION

Accordingly, it is a general object of the present invention to provide an improved composition for pharmaceutical use and a process for preparation of the same.

It is a more specific object of the present invention to provide a pharmaceutical composition containing polypeptides and related proteinaceous materials that is an effective healing agent in the treatment of wounds and maladies occurring at or below the skin surface.

It is a further object of the present invention to provide a pharmaceutical composition to promote healing that can be produced quickly and economically.

A still further object of this invention is to provide a pharmaceutical composition with a wider, more ubiquitous, range of healing applications through its ability to generate and/or stimulate the growth of healthy new tissue.

Additional objects, advantages and novel features of the invention shall be, in part, set forth in the description that follows; in part, will become apparent to those skilled in the art upon examination of the following; and in part, may be learned by the practice of the invention. The objects and the advantages of the invention may be realized and attained by means of the instrumentalities and in the combinations particularly pointed out in the subjoined claims.

To achieve the foregoing and other objects, and in accordance with the purpose of the present invention, as embodied and broadly described herein, the pharmaceutical composition of this invention may comprise an isoelectric casein which is solubilized and accordingly neutralized, by an alkali solution. Said alkali solution preferably comprises potassium hydroxide in conjunction with sodium hydroxide at a molecular weight percentage ratio of potassium hydroxide to sodium hydroxide in the range of 90:10 to 100:0. The casein sol is allowed to equilibrate with the alkali solution for a time sufficient to issue complete neutralization and solubilization of the casein, i.e., in the range of 5 to 35 minutes. The casein is then decomposed through enzyme digestion by the addition of a proteolytic enzyme. Said enzyme digestion is continued for a time sufficient to achieve a preferred level of hydrolysis of the casein into polypeptide chains and related protein fragments. The preferred level of hydrolysis is a partial hydrolysis, such that the weight ratio of protein nitrogen to amino nitrogen is in the range of about 7:1 to 9:1. The time sufficient to achieve this preferred level of hydrolysis varies depending upon the proteolytic enzyme used. However, for the brand used herein, it is roughly in the range of about 1 to 10 minutes, and it was found to be most effective in the range of about 3 to 5 minutes. During digestion the mixture is heated, such that when the time sufficient to achieve the desired level of hydrolysis has expired, the mixture has been heated to the inactivation temperature of the proteolytic enzyme. The resultant improved enzyme-modified casein may be, but does not have to be, mixed with suspending, stabilizing, and preservative agents, which may, for example, be methyl paraben, propyl paraben, caragenan, polyvinyl pyrrolidone (PVP), and aloe vera.

This improved enzyme-modified casein provides an improved composition for pharmaceutical use. It has demonstrated significantly improved healing rates on wounds resulting from traumatic injury. In addition, initial studies have shown the tissue regeneration stimulated by the improved enzyme-modified casein has been found to effect healing of several maladies of the skin, including, for example: infections, such as athlete's foot fungus; burns, including sunburn; dermatitis, such as results from contact with poison ivy; eruptions of the skin, such as cold sores; abrasions; itching; dandruff; and frost bite. Further, there are indications that even when applied topically, the soothing and healing effect of this improved enzyme-modified casein extends to areas directly below the surface of the skin, effecting treatment on, for example: vascular tumors near the skin surface, such as hemorrhoids; sprains; strains; bruises; arthritis, such as Feltes Syndrome; and stiffness.

DETAILED DESCRIPTION OF THE PREFERRED EMBODIMENT

This invention includes a process for the preparation of an improved enzyme-hydrolyzed or modified casein, which demonstrates significantly improved healing rates. The first step in the process is preferably to produce a suitable casein sol, such as from New Zealand Lactic (Trademark). New Zealand Lactic (Trademark) is a casein protein which has an isoelectric point at a pH of about 4.6. At this isoelectric point, the acid and alkaline groups on the protein are equal. Before enzymatic-hydrolysis, the casein is solubilized in water and resultantly neutralized by the addition of alkali solution, such as an alkali metal hydroxide or carbonate. The addition of the alkali solution produces a casein sol with a pH closer to neutral, i.e., about 7.0.

The preferred next step in the process is the enzymatic-hydrolysis of the casein sol. A proteolytic enzyme, such as trypsin, is then added to the neutralized casein sol forming a reacting mixture. The proteolytic enzyme is allowed to react with the casein sol for a time sufficient to digest the casein to a ratio of protein nitrogen to amino nitrogen in the preferred range of about 7:1 to 9:1. This preferred range is considerably narrowed over the prior art, as further experimentation has indicated the ratio of protein nitrogen to amino nitrogen in the range from 7:1 to 9:1 is the level of hydrolysis which is most effective as a healing agent. The point when the casein digestion has reached the level of preferred hydrolysis is measured by time, as determined by prior experimentation. This time sufficient will vary depending on the specific enzyme used, but is usually in the range of 1 to 10 minutes. With Armour's Trypsin (Trademark) or American Lab's Trypsin (Trademark) used in the examples below, a range of 3 to 5 minutes was found sufficient to achieve the preferred level of hydrolysis. The hydrolysis is stopped at the time sufficient by raising the temperature of the reacting mixture to the proteolytic enzyme's inactivation temperature. The inactivation temperature will vary by enzyme, but it was about 140.F for the proteolytic enzymes used in the examples below. When the inactivation temperature is reached, the temperature of the mixture continues to be raised to a level well above the inactivation temperature, for example, 30° to 35° F. above the inactivation temperature, and maintained there for a time sufficient to insure complete inactivation of the enzyme. The time sufficient for inactivation of the enzyme may, for example, be 10 to 30 minutes. Following complete inactivation, an improved enzyme-modified casein sol has been formed and may be cooled.

This pharmaceutical composition can be left and used as a sol. This observation is made because my prior U.S. Pat. No. 3,558,770 described processing the sol of that invention into a dry powder. Such processing was either by freeze drying the enzyme-modified casein sol and then pulverizing it into a powder, or by cooling the enzyme-modified casein sol and then spray drying it into a powder. At that time it was thought that producing a dry powder allowed for the flexibility of marketing the enzyme-modified casein either as a powder for cosmetic uses or as a reconstituted sol for pharmaceutical uses. Research which gave rise to this improved enzyme-modified casein of this invention, indicated that nothing was gained by reducing the enzyme-modified casein sol into a powder and then later reconstituting it into a sol in water. However, there is a great deal to be gained, in terms of time and labor, in not reducing the sol to a powder and then reconstituting it. Avoiding this powder stage reduces production time from days to hours.

Preservative agents, such as Methyl Paraben and Propyl Paraben are then added to the enzyme-modified casein sol to extend and enhance its usable life. The final step is to then pasteurize the sol, thus forming an improved enzyme-modified casein composition.

In addition to the preserving agents, suspending and stabilizing agents, such as polyvinyl pyrrolidone (PVP) and carrageenan, may be added. However, such suspending and stabilizing agents are not necessary. Despite the known healing properties of both PVP and carrageenan, it was found that the improved enzyme-modified casein displayed more significant healing rates than had been observed or achieved before, even without the additions of PVP and carrageenan. This result was not expected from any data previously available. It was known that the most important component contributing to the healing efficiency was the enzyme-modified casein; however, much to my surprise, there appeared to be no significant reduction in healing efficiency with the improved enzyme-modified casein alone, without the carrageenan and PVP. The steps leading to this and other discoveries will be described below.

Also in addition to the preserving agents, Aloe Vera, for example in the form of a 98% pure gel, may be added, just before pasteurizing. Early experimentation, which resulted in this present invention, based, only initially, on the prior art patent, found that adding Aloe Vera gel produced a product with a rusty red color upon pasteurization and which showed signs of certain negative side effects when applied to skin abrasions. It was believed that this red color as well as the negative side effects were the result of a reaction between the Aloe Vera and the polyvinyl pyrrolidone (PVP). Accordingly, in further experimentation, which produced this improved enzyme-modified casein with a more carefully controlled enzymatic-hydrolysis, it was found that the addition of Aloe Vera, without PVP present, produced a product without the rusty red color and that proved an effective healing agent. There was no evidence of the negative side effects initially experienced with a product containing the improved enzyme-modified casein, carrageenan and Aloe Vera. Guinea pigs tested with this product appeared healthy and frisky. The steps leading to this and other discoveries are described below.

One of the first areas of experimentation, in the recent study which developed the present invention, was directed to studying the effect that varying the molecular weight of the PVP would have on the texture of the enzyme-modified casein: The end product, enzyme-modified casein, as disclosed in the prior art, tended to develop a curdy texture with time, which unfortunately presented an untidy and undesirable appearance on the walls of the bottle, and I wanted to eliminate that problem, if possible. The PVP used in the prior art had been a high molecular weight PVP, formed from a mixture of a high molecular weight PVP (K90) and a low molecular weight PVP (K30). The offending bottles all contained preparations with a sizeable proportion of the higher molecular weight PVP (K90). Accordingly, experiments were conducted, reducing the K90 and adding a medium weight PVP (K60). Much of the curdy texture was eliminated by this reduction of the molecular weight of PVP. The preferred ratio was found to be 30 grams K30, 30 grams K60, plus 10 grams K90. However, despite the cosmetic improvement on the improved enzyme-modified casein, no correlation was found between the presence of PVP, quantity of PVP, or the molecular weight of PVP and the healing efficiencies of the improved enzyme-modified casein.

During further experimentation, which developed the present invention, several seemingly innocuous and yet strikingly significant improvements were discovered. It was discovered that in the initial neutralization of casein by the alkali solution, that allows the alkali and casein to equilibrate for a longer period of time, which, for example, may be between 20 to 35 minutes, after an initial 5 minutes of mixing produced a sol which was markedly stiffer than the sol experienced in prior art preparations. This additional equilibrium time of the present invention produces a sol which can barely be rotated with a powerful electric stirring device, but when heated to 145° F., returns to a fluid and workable state. However, it was discovered that the significance of this longer equilibrium time is not the stiffness of the initial sol, but that this longer equilibrium time somehow produces an improved enzyme-modified casein, which healed wounds resulting from traumatic injury in a much shorter period of time.

The improved enzyme-modified casein composition is a gelatinous sol, which may contain carrageenan as a stabilizer. Carrageenan gels show marked differences depending upon the cation with which they are prepared. Using a potassium cation, $K^+$ with carrageenan, produces a strong gel, similar to an agar. Using a sodium cation, $Na^+$, produces a more viscous solution. Armed with this knowledge, additional experimentation which resulted in the present invention was begun using different alkali solutions in the initial step of neutralizing the casein.

Initially, sodium hydroxide was used in place of the potassium hydroxide; however, this proved very ineffective. With sodium hydroxide alone, much of the colloidal material precipitated out of the sol before and after pasteurization. It is believed that the sodium cation caused some of the casein to become unreactive when treated with the proteolytic enzyme. This observation was the first clue that what began as a series of experiments merely to improve the gelatious properties of the end product, enzyme-modified casein composition, more significantly showed that changing or modifying the alkali might substantially effect the quality and quantity of the polypeptide and related protein fragments produced in the enzyme digestion.

Accordingly, several experimental runs were conducted which used sodium hydroxide in conjunction with potassium hydroxide at varying molecular weight ratios. It was found that increasing the potassium hydroxide, decreasing the sodium hydroxide and thereby increasing the potassium to sodium ratio produced much less precipitation. At a ratio of molecular weight percentage of 90:10, potassium hydroxide to sodium hydroxide, virtually no precipitation occurred and there was no evidence of unreactivity of the casein with the proteolytic enzyme. As with the longer equilibrium time, adjusting the alkali solution used to neutralize the casein was found to produce an end product, i.e., the improved enzyme-modified casein composition, which healed wounds resulting from traumatic injury in a significantly shorter period of time. As with the longer equilibrium time, some wounds healed in $1\frac{1}{2}$ to 2 days, a decrease from the 4 days experienced with the prior art composition. The useable ratio of molecular weight percentage of potassium hydroxide to sodium hydroxide is in the range of 90:10 to 100:0, but is preferable in the range of 90:10 to 95:5.

The improved enzyme-modified casein composition, when prepared as described above, has demonstrated significantly improved healing rates on wounds resulting from traumatic injury. In addition, this improved enzyme-modified casein has been found to be effective in the healing of several maladies of the skin, including, but not limited to: infections, such as athlete's foot fungus; burns, including sunburns; dermatitis, such as results from contact with poison ivy; eruptions of the skin, such as cold sores; abrasions; itching; dandruff; and frost bite. For example, I, the inventor suffered frost bite on one of my ears, following exposure to sub-zero weather. The ear swelled twice its normal size, and caused significant pain so as to interfere with my efforts to sleep. After applying some of the enzyme-modified casein composition, which was prepared as described above, the pain subsided to a point that I was able to sleep. Upon awaking, the swelling was also considerably reduced. Within four (4) to five (5) days the ear lobe peeled, and with the peeling skin went the last evidence of the frost bite.

Further, this improved enzyme-modified casein has been found to possess soothing and healing efficiencies on maladies occuring directly below the surface of the skin, including, but not limited to: vascular tumors near the surface of the skin, such as hemorrhoids; spasms; sprains; bruises, stiffness; and arthritis, such as Feltes Syndrome. Feltes Syndrome is a rare form of arthritis effecting, not the joints, but the flesh directly beneath the skin surface. This syndrome causes capillaries to rupture and therefore the skin in the affected area becomes brownish-black. An older male, who was afflicted with Feltes Syndrome and unable to get any relief or heal the sores with the standard medical treatments existing at that time, requested a sample of this improved enzyme-modified casein composition for trial. The improved enzyme-modified casein composition healed the Feltes Syndrome sores within ten (10) days.

Additional examples of these soothing and healing efficients are provided below in conjunction with the prepatory examples given below. It is to be understood that these examples of healing efficiency are for illustrative purposes only, and are not intended to limit the scope of the invention as herein described or as set forth in the subjoined claims.

While the exact improvement in the healing mechanism resulting from increasing the equilibrium time and changing the neutralizing alkali solution is not yet understood, speculations so far have focused on the nature of the protein fragments resulting from enzyme digestion. For example, proteolytic enzymes digest or decompose proteins by cleaving the amino acid chains into polypetides (chains of amino acids smaller than proteins) and related protein fragments. Trypsin is very specific in its cleavage of the protein molecule. It is possible that extending the equilibrium time and adjusting the alkali solution allows for a more complete neutralization of the casein, which perhaps resultantly affects the trypsin cleavage. Perhaps allowing only 10 to 15 minutes for equilibrium results in only a partial neutralization of the casein, whereas allowing 20 to 35 minutes for equilibrium results in a more complete neutralization. Likewise, adjusting the nature of the alkali solution by including some sodium cations with the potassium cations may also result in a more complete neutralization. While potassium is a larger molecular weight cation than sodium, potassium hydroxide has a smaller radius than sodium inasmuch as the electron layer is less viscous than that of sodium, thus enabling potassium to penetrate into smaller spaces along the amino acid chain. The sodium ion on the other hand is a more viscous cation. This more complete neutralization, if that is indeed what is happening, may allow the trypsin to cleave the casein into more uniform polypetide chains and protein fragments or conversely may allow the trypsin to cleave the casein into a wider variety of polypetide chains and protein fragments. Regardless of which or any of these explanations are correct, the result is an improved enzyme-modified casein composition which demonstrates significantly improved healing efficiencies.

Much of the speculation regarding the mechanisms of extending the equilibrium time and adjusting the alkali solution and how these affect healing may not be fully resolved until the mystery surrounding how polypetide chains and protein fragments trigger healing is resolved. When polypetide chains and protein fragments, commonly referred to as growth factors, are applied to wounds or infections, their presence seem to cause cells to multiply much faster and, accordingly, speed the healing process. Some of these polypetide chains and protein fragments seem to stimulate new tissue growth while others seem to stimulate blood vessel regeneration. The exact method of stimulation, and whether these polypetide chains and protein fragments merely stimulate or actually contribute to the new tissue growth, is not yet fully known.

Numerous experimental runs were made in developing, refining and testing this improved healing composition employing an improved enzyme-modified casein, several of which are described below as preparatory examples. It is to be understood that these examples given below are for illustrative purposes only, and are not intended to limit the scope of the invention as herein described or as set forth in the subjoined claims.

EXAMPLE I

An improved enzyme-modified casein composition containing both carrageenan and polyvinyl pyrrolidone (PVP) was prepared with an extended equilibrium time as follows: 150 grams of New Zealand Lactic (Trademark) Casein was added to 185 milliliters of distilled water along with 140 milliliters of potassium hydroxide (KOH 1N) forming a casein suspension. The casein suspension was thoroughly mixed for 5 minutes, then allowed to stand and equilibrate for 25 minutes, at the end of which time the suspension was noticeably stiff. The suspension was then warmed to 145° F., immediately cooled to 115° F. and mixed for an additional 15 minutes.

A dispersion of 0.15 grams of Armour's (Trademark) Trypsin in 15 milliliters of water was then added to the casein suspension. The Trypsin was added to the suspension while the suspension was at 115° F. The resultant mixture of trypsin and casein suspension was heated such that it reached the inactivation temperature of the trypsin, 140° F., after 3 minutes. The heating then continued until the mixture was between about 170° F. to 175° F. and it was held at that level for 20 minutes. This formed an improved enzyme-modified casein sol. Following the 20 minutes, the improved enzyme-modified casein sol was allowed to cool to 140° F.

Meanwhile a PVP-carrageenan solution was prepared by adding 30 grams of K30 (Povidone) and 0.5 grams of carrageenan and mixing thoroughly. To this mixture was then added 67 grams of K60 (45% solution) and 10 grams of K90 and also mixed thoroughly. Finally, this mixture of 3 PVP's and carrageenan was mixed into 500 milliliters of water.

Likewise, a paraben solution was prepared by mixing 1.5 grams of methyl paraben, 0.35 grams of propyl paraben and 1000 milliliters of water. This paraben solution was then heated to 140° F. After which it was combined with the PVP-carrageenan solution forming a stabilizing and preserving solution.

Finally, the improved enzyme-modified casein sol was combined with the stabilizing and preserving solution and heated to 185° F. and held for 20 minutes. This formed the improved enzyme-modified casein composition. After cooling to 170° F, the improved composition was bottled in plastic bottles.

The improved enzyme-modified casein composition of Example I, was found to be extremely effective in healing wounds resulting from traumatic injury. Volunteers which made daily applications of the improved enzyme-modified casein composition to various wounds experienced healing in two days as opposed to the four days healing experienced with prior art compositions.

EXAMPLE II

An improved enzyme-modified casein composition prepared without benefit of carrageenan or polyvinyl pyrrolidone, but with an extended equilibrium time, was prepared as follows: 150 grams of casein was added to 185 grams of distilled water and 140 grams of potassium hydroxide KOH 1N and mixed for 5 minutes forming a casein suspension. The casein suspension was held and allowed to equilibrate for 25 minutes. At which time, it was warmed to 145° F. and then immediately cooled to 115° F. At 115° F., the casein suspension was mixed for an additional 30 minutes.

A dispersion of 0.15 grams of American Lab's (Trademark) Trypsin in 15 milliliters of distilled water was added to the 115° F. casein suspension. The resultant mixture of trypsin and casein suspension was heated such that the inactivation temperature of the trypsin, 140° F., was achieved after 3 minutes. The heating continued until a temperature between about 170° F. and 175° F. was reached, and it was then held at that level for 30 minutes. This formed an improved enzyme-modified casein sol. The casein sol was then diluted with 1050 milliliters of water and mixed with 1 gram methyl paraben and 0.25 grams of propyl paraben. The final step was to heat the entire mixture to 185° F., after which it was cooled to 170° F. and bottled in 2 ounce plastic bottles.

EXAMPLE III

An improved enzyme-modified casein composition containing both carrageenan and polyvinyl pyrrolidone (PVP) was prepared with an extended equilibrium time as follows: 150 grams of New Zealand Lactic (Trademark) Casein was added to 185 milliliters of water along with 140 milliliters of potassium hydroxide (KOH 1N), forming a casein suspension. The casein suspension was mixed for 5 minutes and then held and allowed to equilibrate for 25 minutes. The casein suspension was then warmed to 145° F., immediately cooled to 115° F. and mixed for an additional 15 minutes.

A dispersion of 0.15 grams of Armour's (Trademark) Trypsin in 15 milliliters of water, was then added to the casein suspension, while still at 115° F. The resultant mixture of trypsin and casein suspension was heated so that the inactivation temperature of the trypsin, 140° F., was reached after 3 minutes. Additional heat was added, bringing the mixture to between 170° F. and 175° F., at which temperature it was held for 20 minutes, thus forming an improved enzyme-modified casein sol. The improved enzyme-modified casein sol was then allowed to cool to 140° F.

Meanwhile, a PVP-carrageenan solution was prepared by adding 30 grams of K30 (Povidone) and 0.5 grams carrageenan together and mixing well. Then 67 grams of K60 (45% solution) and 10 grams K90 were added and mixed. Finally, this was diluted with 1000 milliliters of water, thus forming the PVP-carrageenan solution.

A paraben solution was prepared by mixing 2.0 grams of methyl paraben and 0.5 grams of propyl paraben with 500 milliliters of water, and then warming it to fully dissolve the paraben.

The improved enzyme-modified casein sol, the PVP-carrageenan solution and the paraben solution were combined, forming the improved enzyme-modified casein composition. The improved enzyme-modified casein composition was then bottled in glass bottles and pasteurized at 185° F. for 20 minutes.

The improved enzyme-modified casein of Example III was found very effective against athlete's foot and sunburns. One volunteer, a young male had for years suffered with athlete's foot fungus, which resulted in a great deal of peeling and pitted scaring of the feet and a rather strong odor. Other topical lotions and antibiotics prescribed by medical doctors provided only temporary and ineffective reductions in the problem. Within two days of use of the improved enzyme-modified casein composition of Example III, the odor was gone and the peeling and pitting showed signs of healing. After three weeks of topical use, twice per day, all odor, peeling and pitting problems were gone. As of six months after use of the improved enzyme-modified casein composition of Example III, the problem had not returned.

Another volunteer, an older male had suffered from athlete's foot for 15 years. The improved enzyme-modified casein of Example III, was applied topically twice each evening before retiring and each morning the feet were washed, without benefit of treatment. The foot odor disappeared within one day. The intense yellow color of the toenails and cracks in the skin of the feet cleared up by the third day. After one week there was no sign of any athlete's foot, and the problem has not returned to date.

Additionally, the first volunteer, the young male, received a severe sunburn accompanied by a temperature and chills. It was uncomfortable for him to wear clothes or lie down. The improved enzyme-modified casein composition of Example III was applied topically before bed, and the volunteer was able to sleep fairly comfortably. Several more applications the following day and the stinging and soreness disappeared. Within several days, the volunteer had a beautiful tan, which did not peel.

In addition, this improved enzyme-modified casein composition of Example III was also found to be very effective against the itching and scaling of dandruff and the itching and redness of dermatitis as induced by exposure to poison ivy. One male volunteer, who suffered from the itching and falling scales of dandruff, applied a solution of one part the improved enzyme-modified casein composition of Example III and three parts water to his scalp just before retiring for three succeeding nights. After the third night, the scalp had become clear, with no itching, and no signs of scaling or flaking. After the third application, treatment was discontinued. The scalp remained clear and itch free for seven days after discontinuing treatment. On the eighth day, some of the itching had returned, and by the tenth day some scaling and flaking had returned. It appears that the improve enzyme-modified casein composition of Example III, when diluted with shampoo, should help control dandruff, even when only used once a week.

Another male volunteer contracted dermatitis around his eyes due to exposure to poison ivy. This volunteer made several applications of the improved enzyme-modified casein composition of Example III to the affected area. With this treatment, the dermatitis was completely healed within three days.

EXAMPLE IV

An improved enzyme-modified casein composition containing carrageenan, in which the casein was initially neutralized with a mixture of 90:10 molar percent ratio of potassium hydroxide to sodium hydroxide and then allowed an extended equilibrium time was prepared as follows: A solution of sodium hydroxide (1N $N_aOH$) was prepared by dissolving 8 grams of sodium hydroxide in 200 milliliters of water. Likewise, a solution of potassium hydroxide (1N KOH) was prepared by dissolving 10.09 grams of potassium hydroxide in 200 milliliters of water. Then 14 milliliters of the sodium hydroxide solution was added to 126 milliliters of the potassium hydroxide solution, forming 140 milliliters of a potassium-sodium solution at a molar percent ratio of 90:10, potassium hydroxide to sodium hydroxide.

The 140 milliliters of potassium-sodium solution was then added to a loose casein dispersion composed of 150 grams of casein and 185 milliliters of distilled water, thereby forming a casein suspension. The casein suspension was mixed for 5 minutes and then held and allowed to equilibrate for 25 minutes. It was then heated to 145° F. and immediately cooled to 115° F. At 115° F., 0.15 grams Armour (Trademark) Trypsin was added to the casein suspension. The resultant mixture of trypsin and casein suspension was heated such that the inactivation temperature of the trypsin, 140° F., was reached in 4 minutes and 15 seconds, thus forming an improved enzyme-modified casein sol.

Meanwhile, a paraben solution was formed by adding 1.5 grams of methyl paraben and 0.5 grams of propyl paraben to 450 milliliters of water and warmed to dissolve the paraben. Likewise, a carrageenan solution was prepared by adding 0.5 grams of carrageenan to 450 milliliters of distilled water and warmed to disperse.

The improved enzyme-modified casein sol, the paraben solution, and the carrageenan solution were combined and mixed thoroughly, forming an improved enzyme-modified casein composition. Finally, the improved enzyme-modified casein composition was bottled and pasteurized by heating the bottles to 190° F. for 30 minutes.

EXAMPLE V

An improved enzyme-modified casein composition containing carrageenan and polyvinyl pyrrolidone (PVP), in which the casein was initially neutralized with a mixture of 95:5 molar percent ratio of potassium hydroxide to sodium hydroxide, was prepared as follows: A solution of sodium hydroxide (1N NaOH) was prepared by dissolving 2 grams of sodium hydroxide in 50 milliliters of water. Similarly, a solution of potassium hydroxide (1N KOH) was prepared by dissolving 11.2 grams of potassium hydroxide in 200 milliliters of water. Then, 7 milliliters of the sodium hydroxide solution was added to 133 milliliters of the potassium hydroxide solution, forming 140 milliliters of a potassium-sodium solution at a molar percent ratio of 95:5, potassium hydroxide to sodium hydroxide.

The 140 milliliters of potassium-sodium solution was added to 185 milliliters of distilled water along with 150 grams of New Zealand (Trademark) Casein, thereby forming a casein suspension. The casein suspension was mixed for 5 minutes at room temperature and then held and allowed to equilibrate for 6 minutes. The thickness of the casein suspension was noted at several points during the 6 minute equilibrium time: At 3 minutes the suspension was showing signs of becoming quite thick; at 5 minutes the suspension was very thick; at 6 minutes the suspension was thick enough that it was heated to 145° F. to loosen it up and allow for additional mixing. At 145° F., the suspension was immediately cooled to 115° F. and held for an additional 15 minutes with intermittent mixing.

Following this 15 minute period, 0.15 grams of Armour (Trademark) Trypsin was added to the casein suspension. The resultant mixture of trypsin and casein suspension was heated such that the inactivation temperature of the trypsin, 140° F., was achieved in 4 minutes and 15 seconds. The heating was continued until the mixture reached 170° F., thereby forming an improved enzyme-modified casein sol.

Meanwhile, a PVP-carrageenan solution was prepared by adding together 30 grams of K30 (Povidone), 0.5 grams of carrageenan, 67 grams K60 (45% solution), 10 grams of K90, with 900 grams of water. The PVP-carrageenan solution was then heated and stirred to dissolve all its solid elements. A paraben solution was also prepared by adding 2.8 grams of methyl paraben and 0.6 grams of propyl paraben to 400 milliliters of water and then warming and stirring it to fully dissolve the paraben.

The improved enzyme-modified casein sol was combined with the PVP-carrageenan solution and the paraben solution, forming an improved enzyme-modified casein composition. The improved enzyme-modified casein composition was next bottled in 4 ounce amber glass bottles and then heated within the bottles to 190° F. for 30 minutes.

The improved enzyme-modified casein composition of Example V was found to heal wounds resulting from traumatic injury very fast. A volunteer, male, suffered two paper cuts. Applying the improved enzyme-modified casein composition to one cut caused it to heal in half a day, as compared to 1½ days to heal the untreated cut.

EXAMPLE VI

An enzyme-modified casein composition containing carrageenan and polyvinyl pyrrolidone (PVP), which essentially followed the teachings of prior art, was prepared as follows: 150 grams of New Zealand Lactic (Trademark) Casein was added, along with 140 milliliters of potassium hydroxide (1N KOH), to 185 grams of distilled water, thus forming a casein suspension. The casein suspension was mixed thoroughly for 5 minutes and then held for 5 minutes; after which time it was warmed to 145° F. and then immediately cooled to 115° F. The casein suspension was then mixed for an additional 30 minutes at 115° F.

Following the 30 minutes of mixing, 0.15 grams of Armour's (Trademark) Trypsin was added to the casein suspension. The resultant mixture of trypsin and casein suspension was heated so that it reached 140° F., the inactivation temperature of the trypsin, in 5 minutes and 15 seconds. Heating continued until a temperature of 170° F. was reached, thus forming an enzyme-modified casein sol.

A PVP-carrageenan solution was formed by adding 20 grams K90, 0.5 grams carrageenan and 55 grams K30 powder to 630 milliliters of distilled water, then heating and stirring it until the solids dissolved. Likewise, a paraben solution was formed by adding 2.8 grams of methyl paraben and 0.6 grams of propyl paraben to 400 milliliters of water and then warming them to dissolve the paraben.

The three solutions, the enzyme-modified casein sol, the PVP-carrageenan solution, and the paraben solution, were combined together forming an enzyme-modified casein composition. The enzyme-modified casein composition was then bottled in 4 ounce amber glass bottles and heated in the bottles to 190° F. for 30 minutes.

EXAMPLE VII

An improved enzyme-modified casein composition containing both carrageenan and polyvinyl pyrrolidone was prepared with extended equilibrium time as follows: 150 grams of New Zealand Lactic (Trademark) Casein was added, along with 140 milliliters of potassium hydroxide (1N KOH), to 185 milliliters of distilled water, forming a casein suspension. The casein suspension was then mixed for 5 minutes at room temperature and then held for 25 minutes at room temperature to allow the casein suspension to equilibrate. Following which, the casein suspension was then warmed to 145° F. and immediately cooled to 115° F., at which temperature the casein suspension was held for an additional 15 minutes with intermittent mixing. To this casein suspension 0.15 grams Armour's (Trademark) Trypsin was added and the whole thing heated so that a temperature of 140° F., the inactivation temperature of the trypsin, was reached in 4 minutes and 15 seconds. The heating was continued until a temperature of 170° F. was reached; thus forming an improved enzyme-modified casein sol.

Meanwhile, a PVP-carrageenan solution was prepared by mixing 30 grams K27 (Povidone), 0.5 grams carrageenan, 67 grams K60 (45% solids), and 10 grams K90, in 900 milliliters distilled water. This PVP-carrageenan solution was then heated and stirred to dissolve the solids. Likewise, a paraben solution was prepared by adding 2.8 grams methyl paraben and 0.6 grams propyl paraben to 400 milliliters of water and warming to dissolve the paraben.

The improved enzyme-modified casein sol, the PVP-carrageenan solution, and the paraben solution were all combined, forming an improved enzyme-modified casein composition. The enzyme-modified casein composition was then placed in 4 ounce amber glass bottles, heated to 190° F. and held at that temperature for 30 minutes.

EXAMPLE VIII

An improved enzyme-modified casein composition containing carrageenan and polyvinyl pyrrolidone (PVP), in which the casein was initially neutralized with a mixture of 97.5:2.5 molar percent ratio of potassium hydroxide to sodium hydroxide, was prepared as follows: A solution of sodium hydroxide (1N NaOH) was prepared by dissolving 1 gram of sodium hydroxide in 50 milliliters of water. Similarly, a solution of potassium hydroxide (1N KOH) was prepared by dissolving 11.2 grams of potassium hydroxide in 200 milliliters of water. Then, 3½ grams of the sodium hydroxide solution was added to 136½ grams of the potassium hydroxide, forming 140 milliliters of a potassium-sodium solution at a molar percent ratio of 97.5:2.5, potassium hydroxide to sodium hydroxide.

The 140 milliliter potassium-sodium solution was combined with 150 grams of New Zealand Lactic (Trademark) Casein and 185 milliliters of distilled water, mixed for 5 minutes and allowed to stand and equilibrate for 6 minutes. At which time, it was warmed to 145° F., immediately cooled to 115° F. and mixed for 30 additional minutes, thus forming a casein suspension.

A dispersion of 0.15 grams of Armour's (Trademark) Trypsin in 15 milliliters of water was added to the casein suspension and heated from the 115° F. to 140° F., the inactivation temperature of trypsin, in 4 minutes and 15 seconds. Heating continued until a temperature of 170° F. was reached, thus forming an improved enzyme-modified casein sol.

A PVP-carrageenan solution was prepared by mixing together 30 grams of K30 (Povidone), 5 grams of carrageenan, 67 grams of K60 (45% solution) and 10 grams of K90 in 900 milliliters of water. The PVP-carrageenan solution was then heated to dissolve all solids. Similarly, a paraben solution was prepared by adding 2.8 grams methyl paraben and 0.6 grams propyl paraben to 400 milliliters of water, and then warming to dissolve the paraben.

The improved enzyme-modified casein sol, the PVP-carrageenan solution and the paraben solution were all combined forming an improved enzyme-modified casein composition and put in 4 ounce amber glass bottles. Lastly, the improved enzyme-modified casein was heated within the bottles to 190° F. and held at that temperature for 30 minutes.

EXAMPLE IX

An improved enzyme-modified casein composition containing carrageenan, in which the casein was initially neutralized with a mixture of 95:5 molar percent ratio of potassium hydroxide to sodium hydroxide, was prepared as follows: A solution of sodium hydroxide (1N NaOH) was prepared by dissolving 2 grams of sodium hydroxide in 50 grams of water. Likewise, a solution of potassium hydroxide (1N KOH) was prepared by dissolving 11.2 grams of potassium hydroxide in 200 milliliters of water. Then, 7 grams of the sodium hydroxide solution was combined with 133 grams of the potassium hydroxide solution, thereby forming 140 milliliters of potassium-sodium solution at a molar percent ratio of 95:5, potassium hydroxide to sodium hydroxide.

The 140 milliliters of potassium-sodium solution was then combined with 150 grams of New Zealand (Trademark) Casein and 185 milliliters of distilled water, mixed for 5 minutes and allowed to stand and equilibrate for 6 minutes; thereby forming a casein suspension. The casein suspension was then warmed to 145° F. and immediately cooled to 115° F., at which temperature it was held and mixed for an additional 30 minutes.

A dispersion of 0.15 grams of Armour's (Trademark) Trypsin in 15 milliliters of water was added to the casein suspension and heated from the 115° F. to 140° F., the inactivation temperature of trypsin, in 4 minutes and 15 seconds. Additional heat was added, raising the temperature to 170° F., thereby forming an improved enzyme-modified casein sol.

Meanwhile, a paraben-carrageenan solution was prepared by mixing 2.8 grams methyl paraben, 0.6 grams propyl paraben, and 0.5 grams carrageenan into 1050 milliliters of water. The paraben-carrageenan solution was then warmed to 140° F. to dissolve all solids.

The paraben-carrageenan solution was combined with the improved enzyme-modified casein sol and mixed, thus forming an improved enzyme-modified casein composition, which was then bottled in 4 ounce amber glass bottles. The improved enzyme-modified casein composition was then pasteurized by heating the bottles to 190° F. for 30 minutes.

The healing efficiencies of several of these enzyme-modified casein compositions described above were tested by an independent testing lab. Five treatment solutions were studied, comparing the healing efficiency of the enzyme-modified casein composition of Example VI, and the improved enzyme-modified casein compositions of Examples VII, VIII and IX, against a control dressing which was a tincture of zephiran chloride. The control dressing was prepared with one part zephiran chloride concentrate 17%, 64 parts alcohol and 63 parts distilled water.

These tests were conducted using forty young adult albino guinea pigs (twenty males and twenty females), weighing between 300 and 350 grams. The forty guinea pigs were quarantined for one week prior to testing to insure that all test animals were healthy. They were then randomly divided into five treatment groups of eight each, with four male and four female per group, and were then assigned numbers by group. During these tests all animals were housed in individual suspended stainless steel wire cages and were offered Purina Guinea Pig Chow (Trademark) and water "ad libitum".

In order to test the healing efficiencies, traumatic injuries were induced in the forty young adult albino guinea pigs. After anesthetizing the animals with Pentobarbitol Sodium, all abdominal hair was removed by a depilatory agent. The abdominal region was then thoroughly rinsed with tap water to remove all traces of depilatory, and the site choosen to receive the traumatic injury was prepared using standard aseptic surgical procedures. Traumatic injuries were then induced in the forty guinea pigs by making similar midline incisions through the epithelial layers of the guinea pigs abdomens using a scapel with a number 15 blade. Care was taken so that each incision was approximately 5 centimeters in length.

The five treatment solutions were applied to the denuded tissue surfaces, one treatment solution for each group of eight guinea pigs. The skin surfaces of each guinea pig were brought into opposition and secured by a 11 mm Nickel-Silver Michel (Trademark) wound clips. Thereafter, and for the first four days the treatment solutions were applied twice daily.

The applications of treatment solutions were by one milliliter disposable syringes, which administered a predetermined volume of one milliliter per application. The applications occurred twice a day, approximately six hours apart, for the first four days. Daily observations were made of each wound, and a photographic record was taken at 4 hours, 2 days, 4 days, 7 days, 11 days and 14 days. The photographs taken on the seventh day were examined and a comparative analysis was made by a Board Certified Dermatologist. The results of the dermatologist's analysis are discussed below. Each of the wounds had healed over by day 11. Following the observations and photographs on day 14, all animals were sacrificed and the wound scar and surrounding tissue were removed and preserved for histological examination.

Three animals, each from different treatment groups, repeatedly pulled out one or more of the wound clips, reopening their wounds. Because these reopened wounds became infected, these three animals were not considered in the comparative analysis made by the Board Certified Dermatologist. These three animals were from the groups treated with the enzyme-modified casein composition of Example VI and the improved enzyme-modified casein compositions of Examples VII and IX.

Two days after surgery, the improved enzyme-modified casein composition of Example IX showed the best results in terms of healing efficiencies on the wounds. The casein composition of Example IX was the one in which the casein had been neutralized with a solution at a 95:5 molar percent ratio, potassium hydroxide to sodium hydroxide, containing carrageenan and no PVP. Example IX's composition maintained this superiority throughout the study. By day seven, when the photographs were taken which were later evaluated by the Board Certified Dermatologist, one of the wounds had totally healed, and several others were very close to being totally healed. The superiority of Example IX's composition reinforces early observations that significant healing rates can be achieved even in the absence of PVP. Further, it indicates that the best alkali solution ratio is 95:5 molar percent ratio, potassium hydroxide to sodium hydroxide.

The enzyme-modified casein compositions which displayed the next best healing efficiencies were the compositions of Examples VI and VII. Example VI's composition had been produced essentially following the teachings of the prior art. Example VII's composition had been prepared with an extended neutralization period and contained PVP and carrageenan. That Example VI's composition performed this well, was not a real surprise, as it is well known that the prior art composition was a good product. In the comparison conducted by a Board Certified Dermatologist which compared the animals of a treatment group with the control group, but made no direct comparison between treatment groups, indicated that Example VI's composition group showed slightly greater consistency against the control group. However, the group treated with Example VII's composition had one animal which had totally healed, where the group treated with Example VI's composition had no animal which had totally healed. In addition, a direct comparison between the group treated with Example VII's composition and the group treated with Example VI's composition, gives a slight edge to Example VII's composition.

Finally, the group treated with Example VIII's composition had the lowest rate of healing efficiencies of all the enzyme-modified casein compositions, and was essentially equivalent to the control group. This confirmed the belief that utilizing an alkali solution with a 97.5:2.5 molar percent ratio, potassium hydroxide to sodium hydroxide, was not the most effective ratio from the alkali solution, in terms of healing efficiency.

Accordingly, a product and a process have been provided which demonstrate significantly improved pharmaceutical uses. It is to be understood that the foregoing is considered as illustrative only of the principles of the invention. Since numerous modifications and changes will readily occur to those skilled in the art, it is not desired to limit the invention to the exact construction and operation shown and described, and accordingly, all suitable modifications and equivalence may be resorted to falling within the scope of the invention as defined by the claims which follow.

The embodiments of the invention in which an exclusive property or privilege is claimed are defined as follows:

1. An improved pharmaceutical composition for use in wound healing containing partially hydrolyzed casein, wherein the improvement comprises:
said casein having been solubilized and neutralized with an alkali solution comprising potassium hydroxide and sodium hydroxide for a time of about 6 to 35 minutes to provide a weight ratio of protein nitrogen to amino nitrogen in the range of about 7:1 to 9:1, said alkali solution having a molar percentage ratio of about 95:5 of potassium hydroxide to sodium hydroxide.

2. The improved pharmaceutical composition of claim 1, which also contains polyvinyl pyrrolidone.

3. The improved pharmaceutical composition of claim 1, which also contains carrageenan.

4. A pharmaceutical composition for use in wound healing comprising a casein which has ben prepared by the steps of adding said casein to an alkali solution wherein said alkali solution is a mixture of potassium hydroxide and sodium hydroxide with a molar percentage ratio of about 95:5, thereby creating a casein suspension, and neutralizing said suspended casein in said alkali solution for about 6 to 35 minutes, then adding a proteolytic enzyme to said neutralized suspension thereby effecting a hydrolysis of said casein to achieve a weight ratio of protein nitrogen to amino nitrogen in the range of 7:1 to 9:1, and inactivating said proteolytic enzyme when said weight ratio has been achieved.

5. The pharmaceutical composition of claim 4, which also contains polyvinyl pyrrolidone.

6. The pharmaceutical composition claim 4, which also contains carrageenan.

7. The pharmaceutical composition of claim 4, which also contains Aloe Vera.

8. A method of treating an open wound resulting from traumatic injury comprising the step of applying to the open wound the pharmaceutical composition of claim 4.

9. A method of treating a malady of the skin selected from the group consisting of infections, burns, eruptions of the skin, abrasions, itching or frost bite comprising the step of applying to the affected skin area the pharmaceutical composition of claim 4.

10. A method of preparing a pharmaceutical composition for use in wound healing, comprising the steps of:

preparing a neutralized suspension of casein by adding casein to an alkali solution to neutralize said casein, said alkali solution having a molar percentage ratio of about 95:5 of potassium hydroxide to sodium hydroxide, and neutralizing said suspended casein for about 6 to 35 minutes;

adding a proteolytic enzyme to said neutralized suspension, thereby effecting a hydrolysis of said casein to achieve a weight ratio of protein nitrogen to amino nitrogen in the range of 7:1 to 9:1; and inactivating said proteolytic enzyme when said weight ratio has been achieved.

* * * * *